United States Patent [19]
Gershfeld et al.

[11] Patent Number: 5,988,875
[45] Date of Patent: Nov. 23, 1999

[54] CALORIMETER AND METHOD FOR SIMULTANEOUS MEASUREMENT OF THERMAL CONDUCTIVITY AND SPECIFIC HEAT OF FLUIDS

[75] Inventors: Norman Gershfeld, Bethesda, Md.; Courtney Mudd, Great Falls, Va.; Albert Jin, Silver Springs, Md.; Kazuhiro Fukada, Tokyo, Japan

[73] Assignee: The United States of America as respresented by the Department of Health and Human Services, Washington, D.C.

[21] Appl. No.: 08/994,230

[22] Filed: Dec. 19, 1997

[51] Int. Cl.$^6$ ............................ G01N 25/18; G01N 25/00
[52] U.S. Cl. ............................ 374/10; 374/44; 73/204.11
[58] Field of Search ................................. 374/10–12, 29, 374/43, 44; 73/204.11, 204.12

[56] References Cited

U.S. PATENT DOCUMENTS

| | | |
|---|---|---|
| 4,059,982 | 11/1977 | Bowman . |
| 4,630,938 | 12/1986 | Piórkowska-Palczwska et al. . |
| 5,005,985 | 4/1991 | Piórkowska-Galeska et al. . |
| 5,112,136 | 5/1992 | Sakuma et al. . |
| 5,335,993 | 8/1994 | Marcus et al. . |
| 5,711,604 | 1/1998 | Nakamura .................................. 374/44 |

OTHER PUBLICATIONS

D. Bertolini, M. Cassettari, G. Salvetti, E. Tombari, and S. Veronesi, "A differential calorimetric technique for heat capacity and thermal conductivity measurements of liquids," *Rev. Sci. Instrum.*, vol. 61, No. 9, Sep. 1990, pp. 2416–2419.

A. Bernasconi, T. Sleator, D. Posseit, and H.R. Ott, "Dynamic technique for measurement of the thermal conductivity and the specific heat: Application to silica aerogels," *Rev. Sci. Instrum.*, vol. 61, No. 9, Sep. 1990, pp. 2410–2426.

C.P. Mudd, N.L. Gershfeld, R.L. Berger and K. Tajima, "A differential heat–conduction microcalorimeter for heat–capacity measurements of fluids," *Journal of Biochemical and Biophysical Methods*, Elsevier Science Publishers B.V., 26 (1993) 149–171.

N.L. Gershfeld, C.P. Mudd, K. Tajima and R.L. Berger, "Critical temperature for Unilamellar Vesicle Formation in Dimyristoylphosphatidylcholine Dispersions from Specific Heat Measurements," *Biophysical Journal*, vol. 65, Sep. 1993, pp. 1174–1179.

*Primary Examiner*—Vit Miska
*Attorney, Agent, or Firm*—Fitch, Even, Tabin & Flannery

[57] ABSTRACT

A method of simultaneously measuring thermal conductivity and heat capacity of a fluid, using a heat conduction calorimeter having a reference fluid in a first cell and a sample fluid in a second cell includes the steps of calibrating the calorimeter using a standard fluid having known thermal conductivity and heat capacity over a range of temperatures and the reference fluid to determine a set of sensitivity parameters, $\{a_n^{ij}\}$, of the calorimeter, wherein the $a_n^{ij}$ are functions of the calorimeter, temperature and the reference fluid; applying a square wave heat pulse to the calorimeter containing said sample fluid and said reference fluid; measuring the thermal response curve to the square wave heat pulse, wherein the thermal response curve is a function of time, temperature of the measurement, thermal properties of the sample fluid, and thermal properties of the reference fluid; reducing the response curve to a set of discrete characteristic parameters, $\{p_n\}$ wherein each pn is a function of time, temperature of the measurement, thermal properties of the sample fluid and thermal properties of the reference fluid; calculating the thermal conductivity and heat capacity of the sample fluid from the $\{p_n\}$ for the sample fluid and the $\{a_n^{ij}\}$ for the calorimeter.

17 Claims, 11 Drawing Sheets

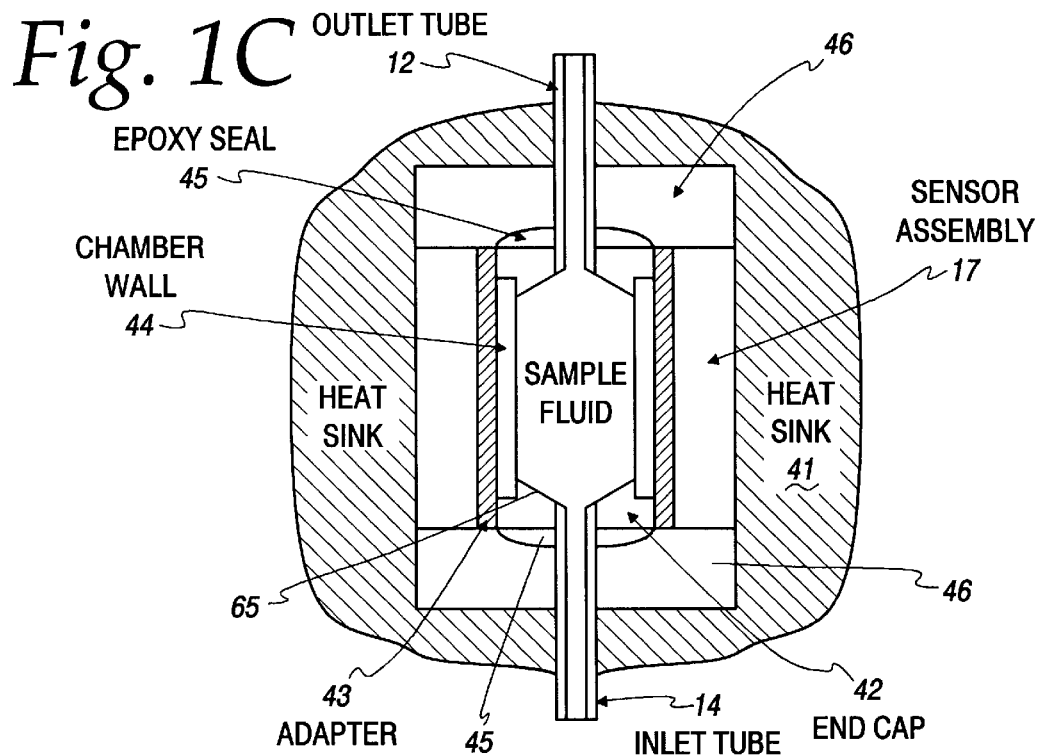
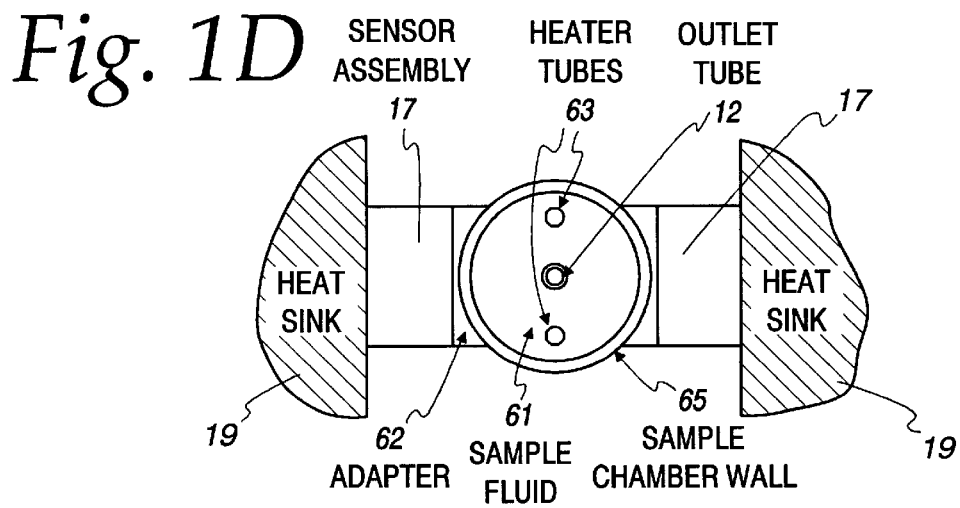
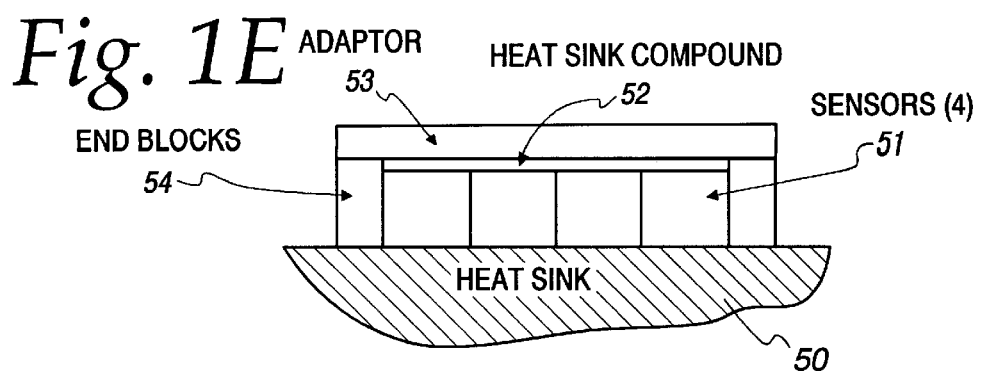

EXCITATION SCHEME FOR CALORIMETER

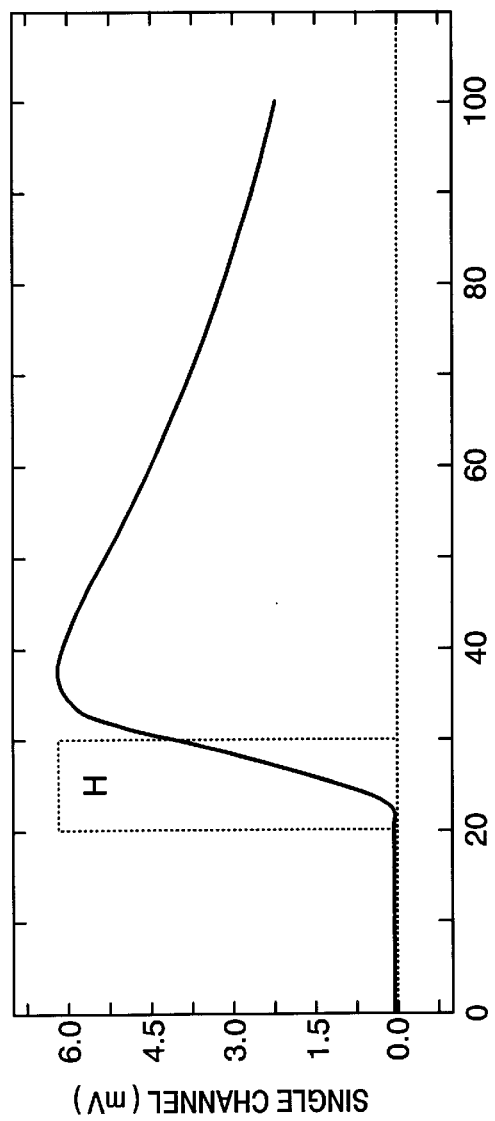
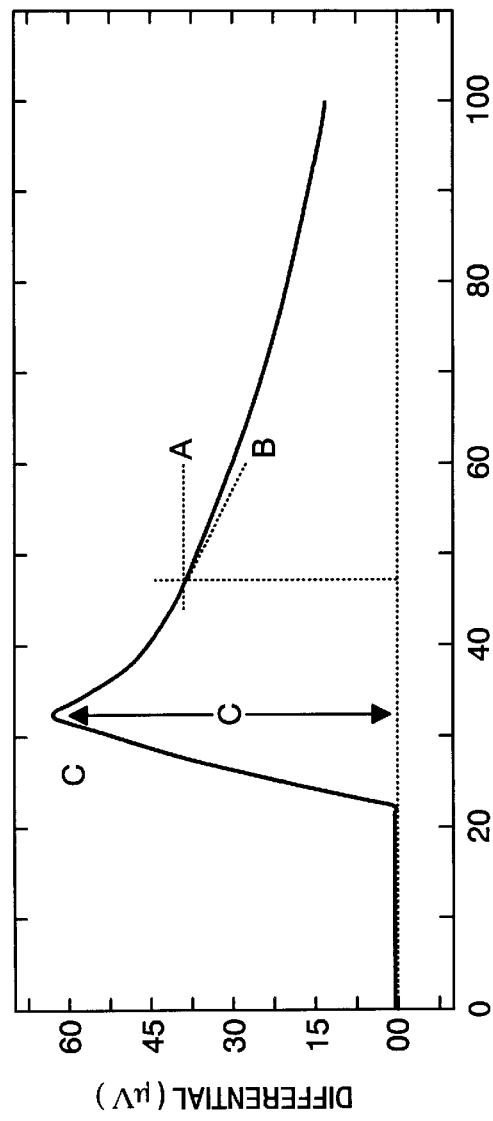
Fig. 2A
Fig. 2B

CALORIMETER AND METHOD FOR SIMULTANEOUS MEASUREMENT OF THERMAL CONDUCTIVITY AND SPECIFIC HEAT OF FLUIDS

BACKGROUND OF THE INVENTION

This invention relates to an apparatus for, and a method of, measuring thermal conductivity ($\lambda$) and heat capacity (C) of fluids, and more particularly, to an excitation/relaxation calorimeter which measures thermal conductivity and heat capacity of a fluid simultaneously.

Measurement of the thermal properties, e.g. thermal conductivity, heat capacity and thermal diffusivity, of materials, including biomaterials, is essential to being able to understand and use them. For example, recent studies of the properties of phospholipid dispersions in water, indicate that a spontaneous transformation from the multilamellar liquid-crystal state to a suspension consisting only of large unilamellar vesicles will occur when the ambient temperature of the dispersion is increased to the transformation temperature. The unilamellar vesicles which form are considered to be a critical state and the thermodynamic properties of the critical unilamellar state indicate the transformation occurs without a latent heat. Such properties have been inferred primarily from measurements of the air/water surface films in equilibrium with the aqueous phospholipid dispersion. There is a need to measure the temperature dependence of the heat capacity of the lipid dispersions directly.

Differential scanning calorimeters, calorimeters which measure the temperature difference between a sample fluid and a reference fluid in response to a temperature scan, have been widely used to investigate the macroscopic properties of matter. However, commercial differential scanning calorimeters have been unable to make such measurements due to the additional constraints inherent in biomaterials in aqueous solutions. Such constraints include irreproducibility of the baseline, the small sample size available (e.g. milligram quantities of membrane materials), filling errors including artifacts from trapped air in the sample chamber, the chamber to sample mass ratio needed to maximize signal sensitivity and a measuring sensitivity of the order of, for example, 400 $\mu$J/° C.·cm$^3$.

C. P. Mudd et al., "A differential heat-conduction microcalorimeter for heat-capacity measurements of fluids," Journal of Biochemical and Biophysical Methods, 26 (1993) 149–171, describe a calorimeter with high sensitivity for measuring the specific heats of fluids. However, that calorimeter does not measure thermal conductivity and heat capacity simultaneously; rather it measures thermal diffusivity (thermal conductivity is known and approximately constant) and calculates heat capacity from the thermal diffusivity relationship:

$$\eta = \lambda / \varrho C_p,$$

where $\eta$ is thermal diffusivity, $\lambda$ is thermal diffusivity and $\varrho C_p$ is the volume heat capacity. Mudd et al.'s calorimeter was designed, in part, because of their discovery that the peak of the response to a brief thermal pulse was approximately four times more sensitive to heat capacity than the thermal conductivity of the aqueous lipid dispersions. By limiting their measurements to a narrow range of fluids, with heat capacities near that of the dilute lipid dispersions and with similar diffusivities, they were able to circumvent approximating the effect of $\lambda$, which in principle may change independently of heat capacity.

Although Mudd et al. avoided measuring $\lambda$ in lipid dispersions, such an assumption cannot be made for all biomaterials. Furthermore, in addition to the relationship between thermal conductivity and heat capacity for a given material, the interplay between heat capacity and thermal conductivity in almost all thermal instruments is a well recognized problem which can affect measurements of the material's properties. Previous efforts in dealing with this problem involve two approaches. In the first approach, the effect of one of the properties is minimized, then the other property is measured. In the second approach, both properties are measured simultaneously. Examples of such approaches can be found in D. Bertolini et al., "A differential calorimetric technique for heat capacity and thermal conductivity measurements of liquids," Rev. Sci. Instrum. 61(9), September 1990, 2416–2419, A. Bernasccni et al., "Dynamic technique for measurement of the thermal conductivity and the specific heat: Application to silica aerogels," Rev. Sci. Instrum. 61(9), September 1990, 2420–2426 and N. Gershfeld et al., "Critical Temperature for Unilamellar Vesicle Formation in Dimyristoylphosphatidylcholine Dispersions from Specific Heat Measurements," Biophysical Journal, 65, September 1993, 1174–1179. Both approaches suffer from limitations of applicable materials, lack of precision or both.

Therefore, it is an object of the invention to provide a calorimeter which measures thermal conductivity and heat capacity simultaneously. It is another object of the invention to provide a calorimeter which minimizes the effects of the thermal conductivity and heat capacity of components of the measurement instrument.

SUMMARY OF THE INVENTION

To achieve the foregoing and other objects, a calorimeter and method of analyzing the dynamic response for ultrasensitive simultaneous measurements of heat capacity and thermal conductivity of fluid is provided. The calorimeter uses the excitation/relaxation method to measure the differential temperature between a sample fluid and a reference fluid in response to a heat pulse. The calorimeter includes cells for the reference fluid and the sample fluid. Each cell includes a chamber, with an internal heater, rigidly positioned between two temperature sensors. The space between the sensors and the chamber has been eliminated to remove air gaps and minimize movement of the components in the sensor pathway. This virtually eliminates any effects associated with manipulation of the solutions. To eliminate air bubbles that form when filling the cells, the fluids are loaded under a partial vacuum, which reduces filling errors to the level of the system noise.

The calorimeter is first calibrated using one or more known standard fluids, i.e. ones with known thermal conductivities and heat capacities over a wide range of temperatures. Calibration provides a series of sensitivity coefficients, representative of the instrument and the reference fluid chosen. Then the differential voltage-time response curve, representing the thermal response to a heat pulse, is reduced to a discrete set of parameters. Thermal conductivity and heat capacity of the sample fluid can then be calculated from the sensitivity coefficients and the parameters. The calorimeter and method of the invention achieve accuracies in the area of one part in ten thousand for heat capacity and thermal conductivity. For repeated measurements of stable samples, the run-to-run variations of the measurement for both the heat capacity and thermal conductivity are about one part in one hundred thousand.

BRIEF DESCRIPTION OF THE DRAWINGS

FIGS. 1A–1F are various views, including a block diagram, of a calorimeter according to the invention;

FIGS. 2A–2B are the single channel and differential channel response for water—water (sample—reference);

DESCRIPTION OF THE PREFERRED EMBODIMENT

Figure 1A:
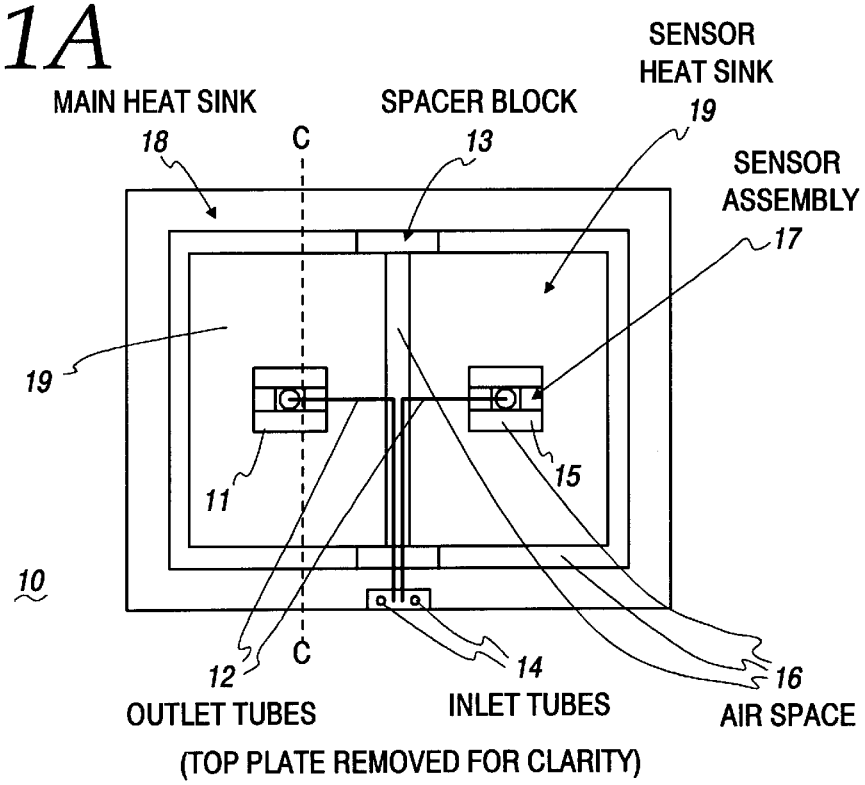
Figure 1B:
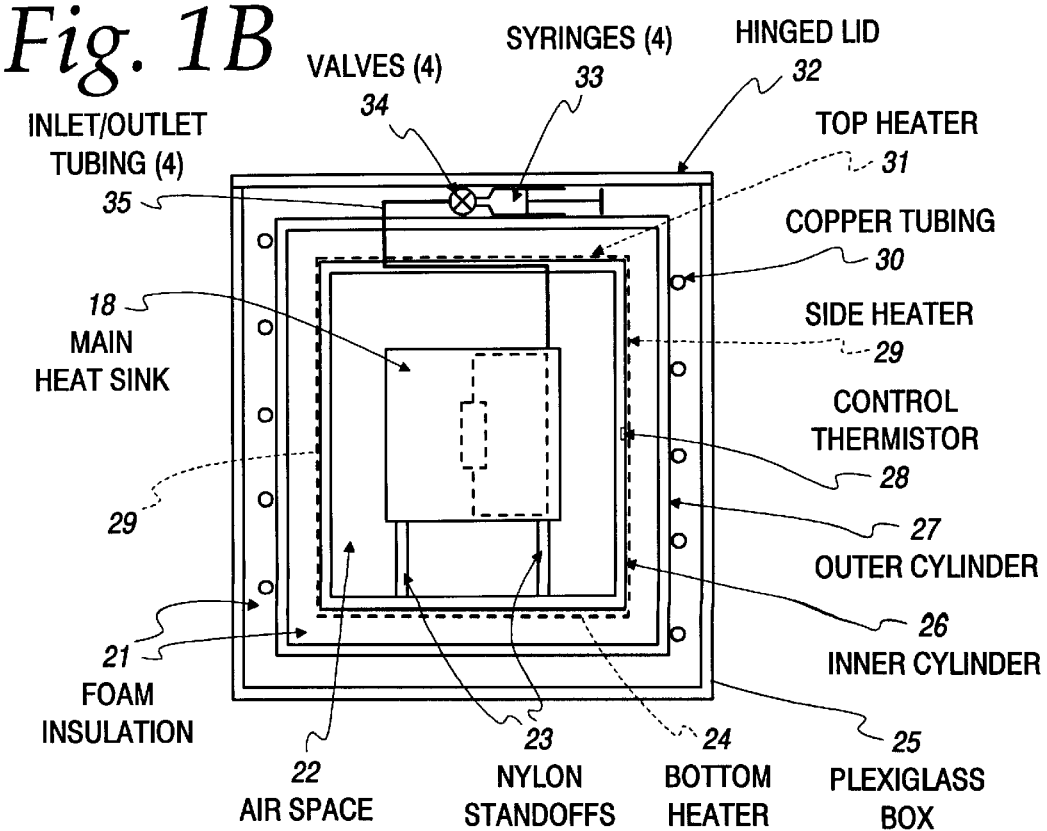

FIG. 1A is a schematic top view and FIG. 1B is a schematic side view of calorimeter which measures thermal conductivity, $\lambda$, and volume heat capacity, $\varrho C_p$, simultaneously. Calorimeter 10 includes cells 11 and 15, preferably formed of tantalum, which are each disposed within heat sink assembly 19. Referring to FIG. 1D, an end view of the chamber assembly, each cell consists of chamber 65 for receiving a fluid. Disposed within chamber 65 are heater tubes 63 for heating the fluid 61. Also disposed within chamber 65 is outlet tube 12 for removal of the fluid. Chamber 65 is disposed between two sensor assemblies 17 via adapter 62 which is formed of copper. Sensor assemblies 17 are rigidly coupled to chamber 65 to minimize movement of the components within the sensor pathway.

FIG. 1C is a cross-sectional side view of cell 11 along line C—C of FIG. 1A. Sample fluid is provided through inlet tube 14 to chamber 65 under partial vacuum to eliminate the air bubbles that usually form when filling the cells.

Preferably, the fluids are loaded under a partial vacuum of about 50 mm Hg (above the vapor pressure of the fluids). After the cells are filled, the pressure in the cells is returned to atmospheric pressure (approximately 760 mm Hg) thereby reducing the volume of any trapped gas bubbles by a factor of about 15. In addition, at 760 mm Hg gas solubility increases thereby further reducing any trapped gas bubbles. Sensor assemblies 17 are disposed at opposite sides of chamber 65, coupled through adapter 43 to chamber walls 44. Epoxy seals 45 are used to seal outlet tube 12 and inlet tube 14 to chamber 65. Cell 11 and sensor assemblies 17 are then placed within heat sink 41. Additional epoxy 46 is used to eliminate air gaps in the system and to rigidly attach the cell/sensor assembly within the calorimeter.

Referring again to FIG. 1A, each cell/sensor assembly (11, 17 and 15, 17) is disposed within main heat sink 18. Cell/sensor assembly (11,17) is separated from cell/sensor assembly (15, 17) by a spacer block, which maintains a space down which inlet tubes 14 are fed into calorimeter 10.

Referring to FIG. 1B, main heat sink 18 is disposed within inner cylinder 26, supported by nylon standoffs 23. Inner cylinder 26 is heated by top heater 31, side heaters 29 and bottom heater 24, which are controlled by thermistor 27. The temperature of the heat sink is set to an accuracy of 0.01 degrees in the range of 0 to 50 degrees Celsius, with a proportional plus integral temperature controller (not shown). After the desired baseline temperature is reached, the controller stability is approximately ±0.001 degrees Celsius. Inner cylinder 26 is disposed within outer cylinder 27, separated by a layer of foam insulation 21. Outer cylinder 27 is disposed within plexiglass box 25, separated by a layer of foam insulation. Hinged lid 32 opens up to permit access to inlet/outlet tubes 35, which are fed through inner and outer cylinders 29, 27 through valves 34. Syringes 33 are used to input the fluid through the inlet tubing. Copper tubing 30 provides additional temperature control at the interface of the outer cylinder 27.

Referring to FIG. 1E, a preferred sensor assembly is shown. Each sensor assembly consists of four sensors 51 disposed between end blocks 54, adaptor 53 and heat sink 50. Heat sink compound 52 thermally bonds sensors 51 to adaptor 53.

Figure 1F:
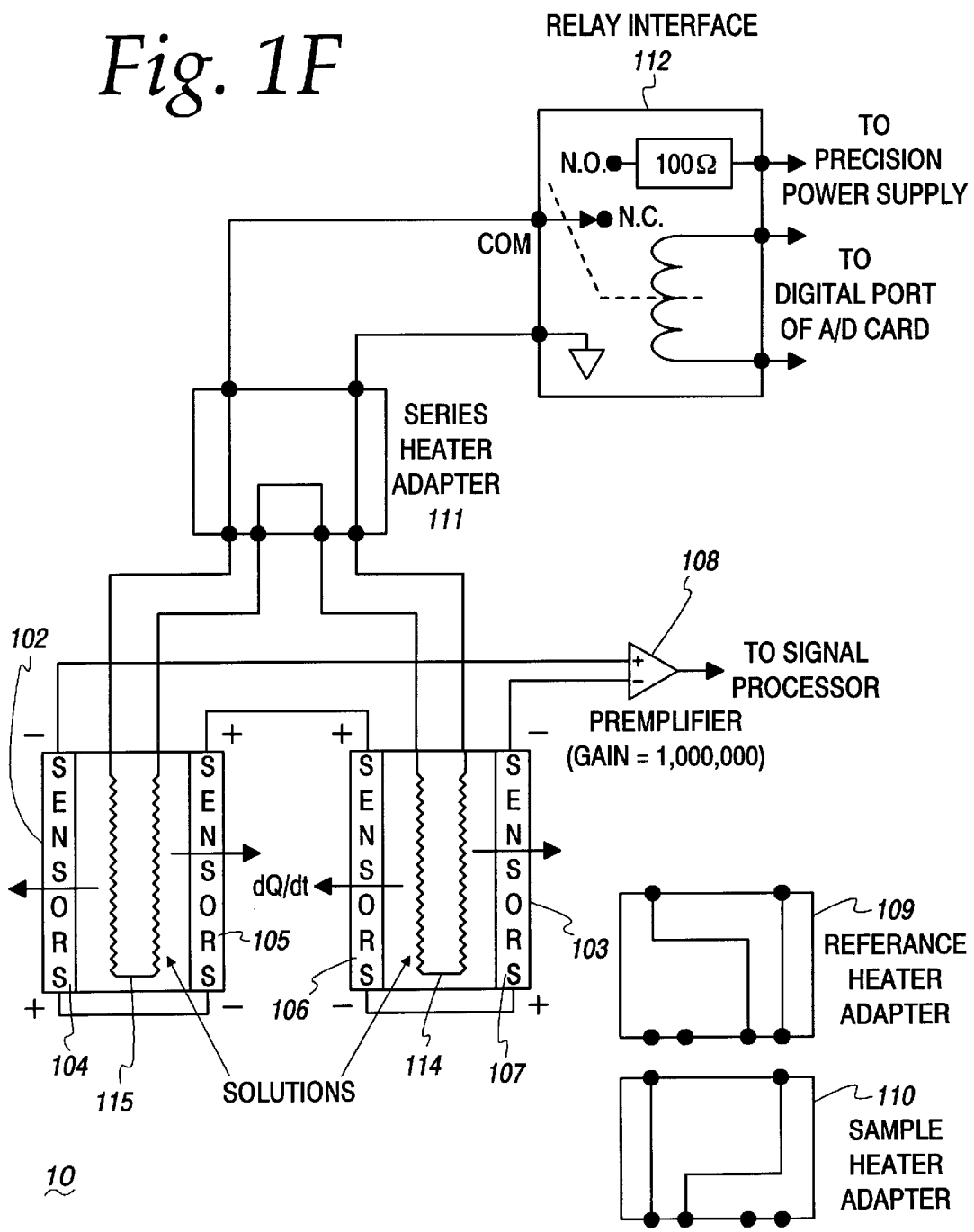

FIG. 1F shows an excitation scheme for calorimeter 10. Calorimeter 10 consists of two tantalum cells 102 and 103 wired in series with each other. One of the cells is filled with the reference material, which is generally pure water. The other cell is filled with the sample fluid. Each cell is sandwiched between two sensor assemblies, (104,105) and (106,107) respectively, each consisting of four thermopiles (not shown). The sensor assemblies are electrically coupled in opposition to measure the difference between cell responses. The outputs of the two cells is input to preamplifier 108 before going to the signal processor (not shown). The electronic noise of the data acquisition system with the sensors shorted was reduced to 2 nV(rms). Preamplifier 108 amplifies the differential sensor signal from cells 102 and 103. With the sensors connected and the system at thermal equilibrium, the overall system noise is 4 nv(rms). Reference heater 109 and sample heater 110 heat cells 102 and 103 to an initial temperature before the test pulse is applied. Series heater adapter 111 applies the excitation (preferably a square wave) heat pulse to the two cells in response to a control signal from relay interface 112.

A NIST traceable digital thermometer (Thermometric model TS8901, with a one year accuracy of ±0.002 degrees Celsius) is placed (not shown) in the main heat sink 18 of the calorimeter to measure the actual core temperature of the heat sink. Test measurements during construction of the calorimeter indicate that the temperature difference between the cell and the location of the digital temperature probe is approximately 50 millidegrees Celsius. The output of the thermometer is recorded via the serial port of a computer before and after each excitation pulse.

The calorimeter of the invention operates on the principle that the thermal response of a fluid sample to a short, for example ten second, electrically generated heat burst in the fluid is a function of the heat properties of that fluid. Thermal response is recorded using an excitation/relaxation cycle that takes, for example, 500 seconds. Baseline data are taken for the first 20 seconds, then the heaters are turned on for 10 seconds. The remainder of the time is used to record the differential peak response and to allow the system to decay back to thermal equilibrium before the next pulse is applied. Since each sensor assembly outputs a voltage signal that is directly correlated to the heat flux through its two parallel surfaces, the amplified response reflects the sample's heat properties for heat adsorption/release (i.e., heat capacity) and conduction (thermal conductivity). Preferably, this response is recorded at 20 samples/second and stored with the core temperature.

Thermal response from the calorimeter is collected in the differential voltage time response curve, V(t), to a square-wave heat pulse. Differential thermal response depends, not only on the thermal properties (thermal conductivity and heat capacity) of the solutions in the sample cells, but also on the physical aspects of the system, such as the physical dimensions of the calorimeter, temperature T, choice of reference solution, and physical matching of the two cells. In general, then, $$V(t) = V(t, \lambda, C, T, \lambda_{ref}, C_{ref}, x, y, z)$$

where t is time, $\lambda$ is the thermal conductivity of the sample, C is the volume heat capacity of the sample, T is the temperature of the measurement, $\lambda_{ref}$ and $C_{ref}$ are the thermal conductivity and volume heat capacity of the reference solution and x,y,z represent the instrument's physical dimensions.

Figure 3:
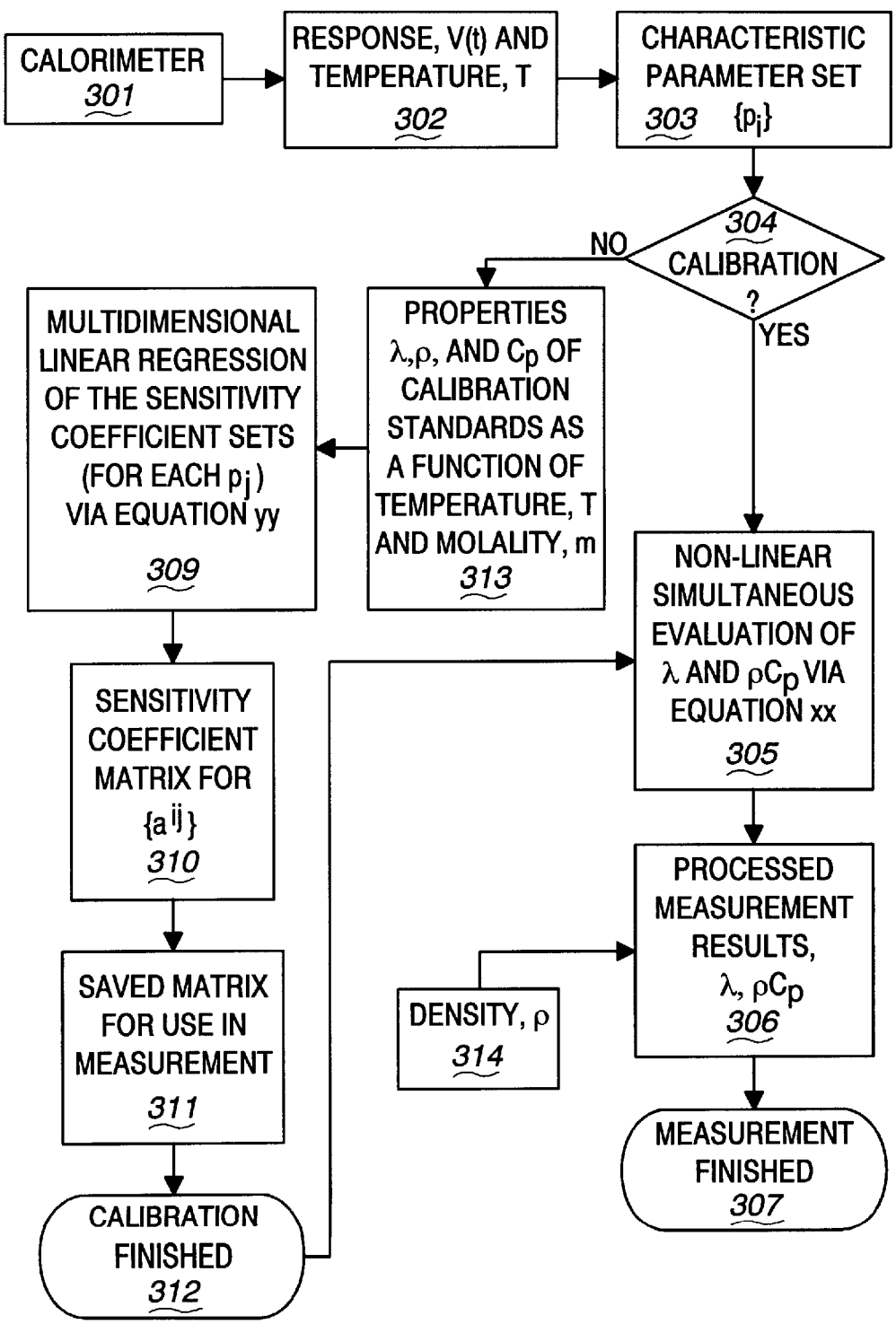
FIG. 3 is a flow diagram of a calibration/measurement scheme.

Quantitatively, it is difficult to establish a useable relationship among so many variables. FIG. 3 shows the calibration and data reduction scheme according to the invention, which enables the simultaneous determination of thermal conductivity and heat capacity for fluids as a function of temperature from each measurement of V(t).

Referring to FIG. 3, calorimeter (301) is used to generate a thermal response, V(t), in response to a square wave heat pulse (302). V(t) is reduced (303) to a set of discrete characteristic parameters, $\{p_n, n=0, 1, \ldots N-1\}$ using the following relationship:

$$p_n = \sum_{i,j=0}^{Q} (a_n^{ij}(T) \Delta C^i \Delta \lambda^j),$$

where $a_n^{ij}(T)$=set of sensitivity coefficients for $p_n$, $\Delta C = (C_{samp}/C_{ref}-1)/100$=percent change from the reference value of C, $\Delta \lambda = (\lambda_{samp}/\lambda_{ref}-1)/100$=percent change from the reference value of $\lambda$, $\lambda_{ref}(T)$=thermal conductivity of the reference as a function of T, and $C_{ref}(T)$=volumetric heat capacity of the reference as a function of T. In addition, $p_n$ may be expressed in closed form equations. If the calorimeter has been calibrated, the method proceeds to block 305 where thermal conductivity and volume heat capacity are calculated in accordance with the following relationship:

$$\sum_{i+j=1}^{Q} (b_n^{ij} \Delta C^i \Delta \lambda^j) = p_n - a_n^{00}(T), \text{ where } b_n^{ij} = a_n^{ij}(T).$$

$\Delta \lambda$ and $\Delta C$ are then determined by solving this set of N expressions. These differences are then converted to (Cp, T) and the transport properties ($\lambda$, T) for the fluid sample using the known properties of the reference solution. Then the measurement is finished (307). If the calorimeter has not been calibrated, calibration begins in block 313 where the calorimeter's set of sensitivity coefficients $\{a_n^{ij}\}$ is calibrated using a standard fluid, whose thermal properties are known for a wide range of temperatures, and the desired reference fluid. The $\{a_n^{ij}\}$ may be computed for each characteristic parameter (309) by applying the multidimensional regression procedure separately at each temperature where thermal conductivity and heat capacity of the standard fluid are known and then completed by extrapolation and interpolation over the temperature range. Once the sensitivity coefficient matrix is determined (311), calibration is completed (312) and the matrix can be applied to step 305 for subsequent measurements of sample fluids.

FIGS. 2A and 2B are graphs of single channel and differential channel response with examples of the characteristic parameters for a water (sample)—water (reference) measurement. The differential response is typically only one hundredth of the single channel response, but it contains much less run-to-run noise due to the common mode rejection of temporal and other noises affecting both channels. The bi-phasic nature of the differential response is typical of systems in which there is a small difference in the time constraints and sensitivities of the two channel responses. Differential response is conveniently described by parameters such as the main peak height, peak position, and response heights at various fixed time grid points.

It is crucial to have an adequate set of discrete parameters $\{p_n\}$ to represent the informational content of the differential response V(t) (0<t<100 s). Initially, the response graph is divided into three regions (FIG. 2B): the nearly flat baseline region, 0<t<20, the rising response region, 20+$\delta$1<t<30+$\delta$2, and the falling or decay relaxation period, 30+$\delta$3<t<100, where the $\delta$1, $\delta$2, $\delta$3 are small offset values. In each of the three regions, V(t) is represented by an n-th order polynomial with a relatively small value of n (typically 3), confirming that both V(t) and the corresponding small set of polynomial curve-fit coefficients contain the equivalent information content. These polynomials produce intersections and yield a special characteristic parameter, such as $pC_0$=initial rising slope–the slope of the rising polynomial at its intersection with the baseline polynomial; $pC_1$=Peak Response ($V_{peak}$)–the response value at the intersection of the rising region and the decay region; $pC_3$=Peak response point–the intersection position for $V_{peak}$. In addition to these parameters, the parameter list has been expanded to include all the time-grid parameters, including both the response values and their slopes at each time step in to the response. Instead of calculating these parameters directly from raw data, polynomials are fit to the raw data in narrow regions around the time grid points and the parameters are calculated from the polynomials. This approach reduces the sensitivity of the parameter calculation to a single outlier data point since the polynomial fits are smooth analytical functions. Thus the polynomial fits provide a degree of noise filtering.

Figure 4:
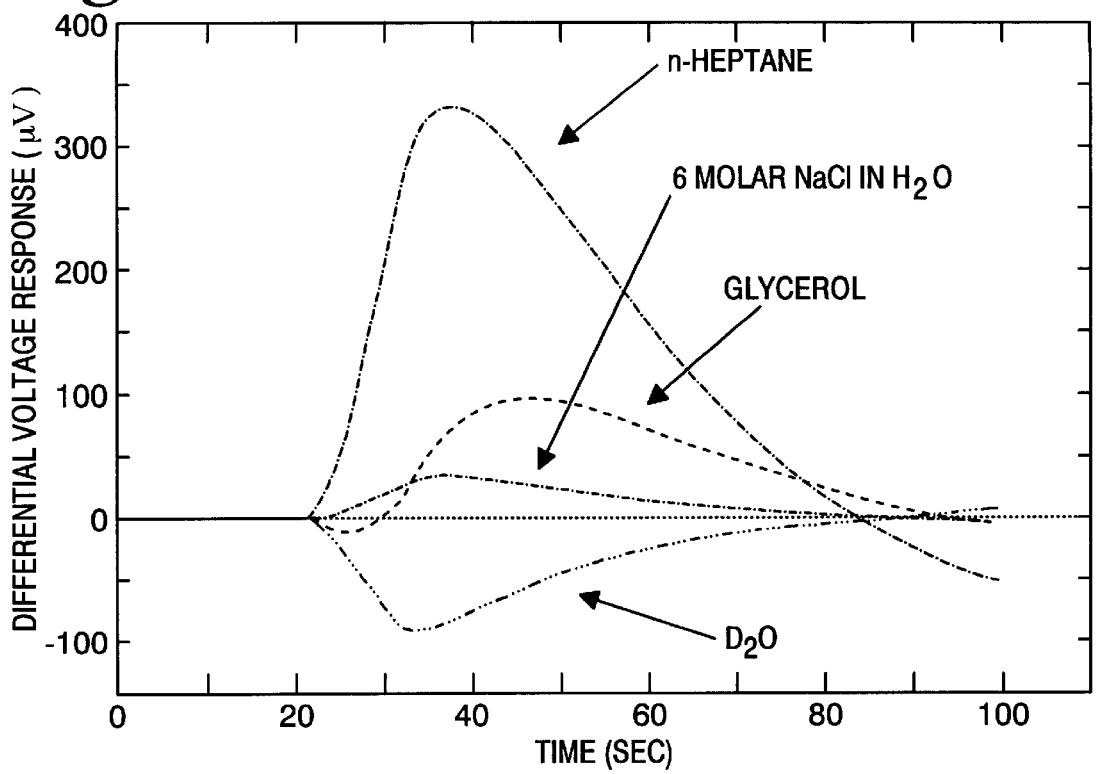
FIG. 4 is a graph of plots of the differential voltage response of selective standard fluids with pure water as the reference fluid.
Figure 5:
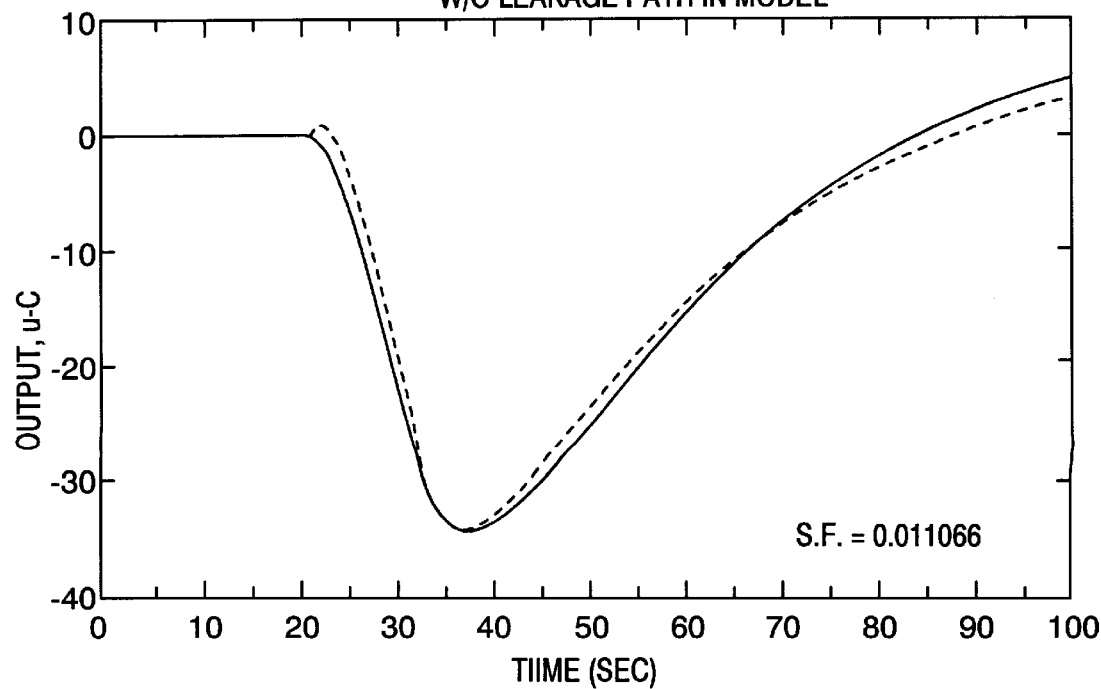
FIG. 5 is a comparison of the thermal output of a simulated response and an actual response for 6 molar NaCl.

FIG. 4 shows the differential responses of four selected standard fluids, n-heptane, 6 molar NaCl in $H_2O$, glycerol and $D_2O$ using the method of the invention to calibrate the calorimeter. FIG. 5 shows a comparison of a simulated response (the solid line) using a R-C model for the instrument and the actual measured response (dashed line) of the standard fluid 6 molar NaCl in pure water versus pure water as the reference fluid. Such close matching suggests the simulated model should qualitatively capture the behavior of the real instrument.

Figure 6A:
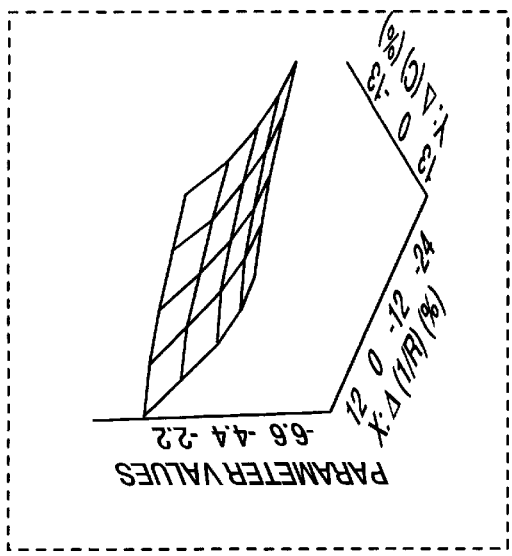
FIGS. 6A–6D are graphs of typical parameter values over a regular ($\Delta C$, $\Delta \lambda$) grid with spine surface connections.
Figure 6B:
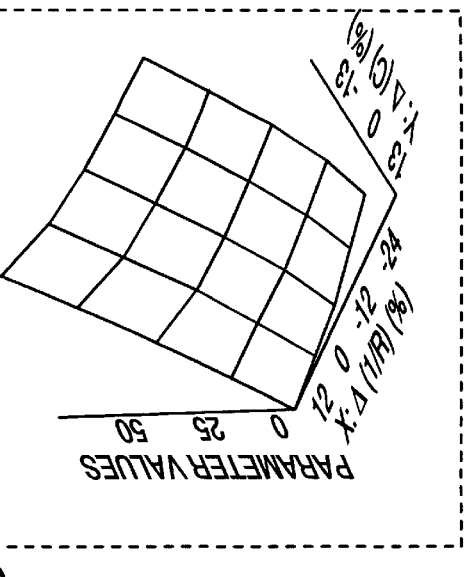
Figure 6C:
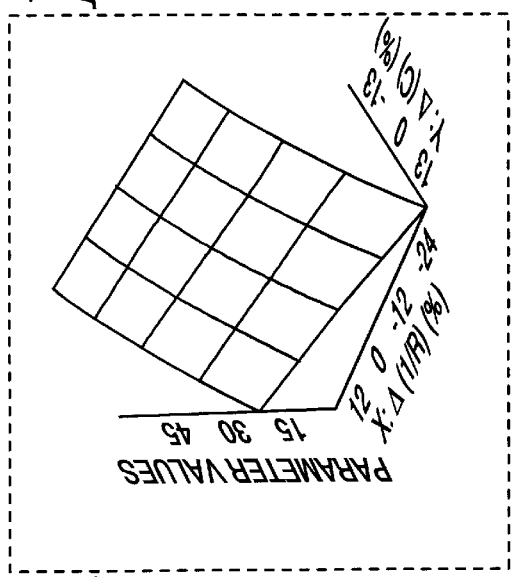
Figure 6D:
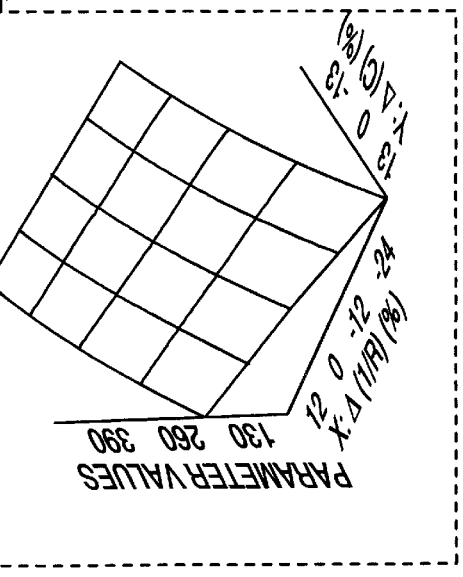

A series of 25 simulations were run over a regular 5×5 grid of values of $\Delta C=\{25,12.5,0,-12.5,-25\}$ and $\Delta \lambda=\{20, 11.1,0,-14.3,-33.3\}$ in percentages of the values corresponding to pure water at 25>), and observed following respective effects on the output response, V(t), and its analysis according to the approach of the invention. Each simulated V(t) provides a complete set of parameters $p_n$ (where N=60, for example) including time-grid parameters and peak heights, etc. Each parameter has 25 values as a function of 25 combinations of $\Delta C$ and $\Delta \lambda$, and thus are conveniently examined by surface plots. FIGS. 6A–6D show surface plots for four typical parameters: peak height in $\mu V$ (FIG. 6A), slope at 65 second grid point in $\mu$V/s (FIG. 6B), response height at 32 second grid point in $\mu$V (FIG. 6C) and response height at 65 second grid point in $\mu$V (FIG. 6D). These surface plots show that the characteristic parameters depend smoothly and nearly linearly on $\Delta C$ and $\Delta \lambda$ over the entire range. This response affirms the notion that the response is well-behaved mathematically and thus amenable to a relatively simple mathematical expression. Specifically, the direct power law expansions should converge for each parameter, in that the fitting residuals should decrease as more and more non-linear high-order terms are included.

Figure 7:
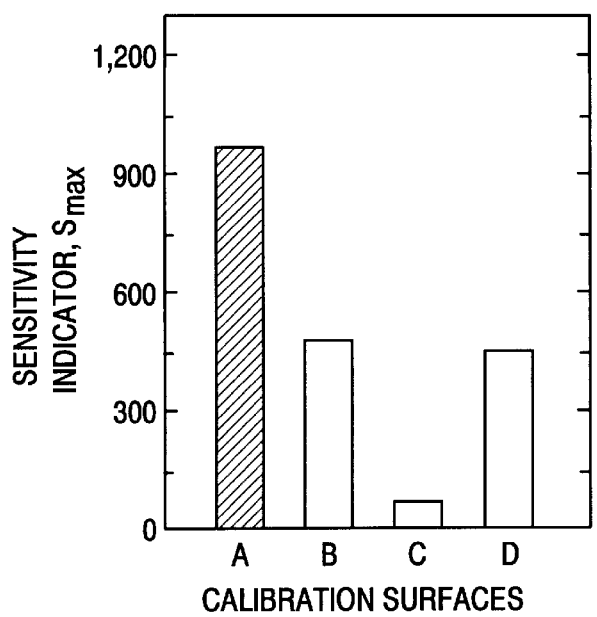
FIG. 7 is a bar chart comparing the maximum value of a sensitivity indicator for several characteristic surfaces.

To compare qualitatively the fitting quality of the discrete parameters, a dynamic-range, dimensionless sensitivity indicator was calculated. FIG. 7 shows the maximum value of the sensitivity indicator for several comparative characteristic surfaces. Bar A corresponds to the preferred surface form; Bar B represents the reductive effect of forcing just one calibration coefficient to zero; Bar C corresponds to linear calibration surfaces which are the same as enforcing both calibration coefficients to zero; Bar D correlates to a direct, fully second power law expansion of the calibration surfaces with three nonlinear terms ($\Delta C^2$, $\Delta C \Delta \lambda$ and $\Delta \lambda^2$).

Figure 8:
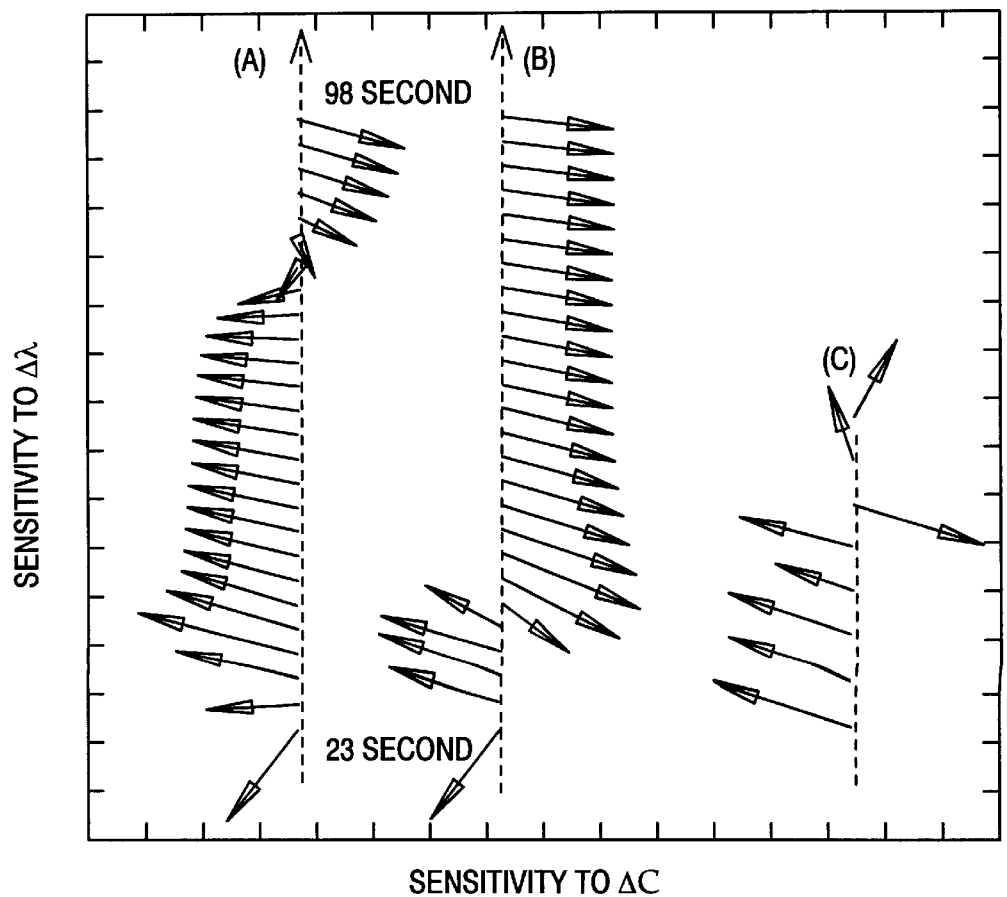
FIG. 8 is a graph of the sensitivity vectors and their magnitudes in log scale for 60 characteristic parameters of a system according to the invention.

Another indication of precision of the simultaneous heat capacity and thermal conductivity measurement is the orthogonality of sensitivity vectors associated with the discrete parameters $\{p_n\}$ The magnitude of the sensitivity vector is simply the sensitivity indicator; the directions of the sensitivity vectors is an indication of the independence of the discrete parameters. FIG. 8 shows both the direction of the sensitivity vectors and their magnitudes (in log scale) for the 60 characteristic parameters in the model described herein. These sensitivity vectors are evaluated at parameter values near the center of the ($\Delta C$, $\Delta \lambda$) simulation grid. Since all parameters have calibration surfaces that are fairly flat, this map of sensitivity vectors do not change significantly at other locations. Since the vectors are plotted with their lengths equal to logarithmic of their magnitudes, the parameters vary significantly in their resolution indicator values. FIG. 8 shows that the model system parameters have both high sensitivity indicator of about 1000 and they are quite orthogonal with mutual vector angles of at least 15 degrees. Specifically, FIG. 8 shows the sensitivity vectors for the 60 parameters of the R-C simulation model for the calorimeter. The 26 response height parameters $\{pA\}$, 26 slope parameters $\{pB\}$, and 8 special polynomial fitting parameters are described above with reference to FIG. 2 (above). The direction of each vector shows the relative sensitivity toward a heat capacity change ($\Delta C$) and a thermal conductivity change ($\Delta \lambda$) for the corresponding characteristic parameters. This indicates that the relative uncertainties for many individual solutions of the parameter equations are likely lower than about $\frac{1}{250}$. With further improvement expected from statistical averaging, this confirms the level of precision for the calorimeter and method of the invention.

Figure 9:
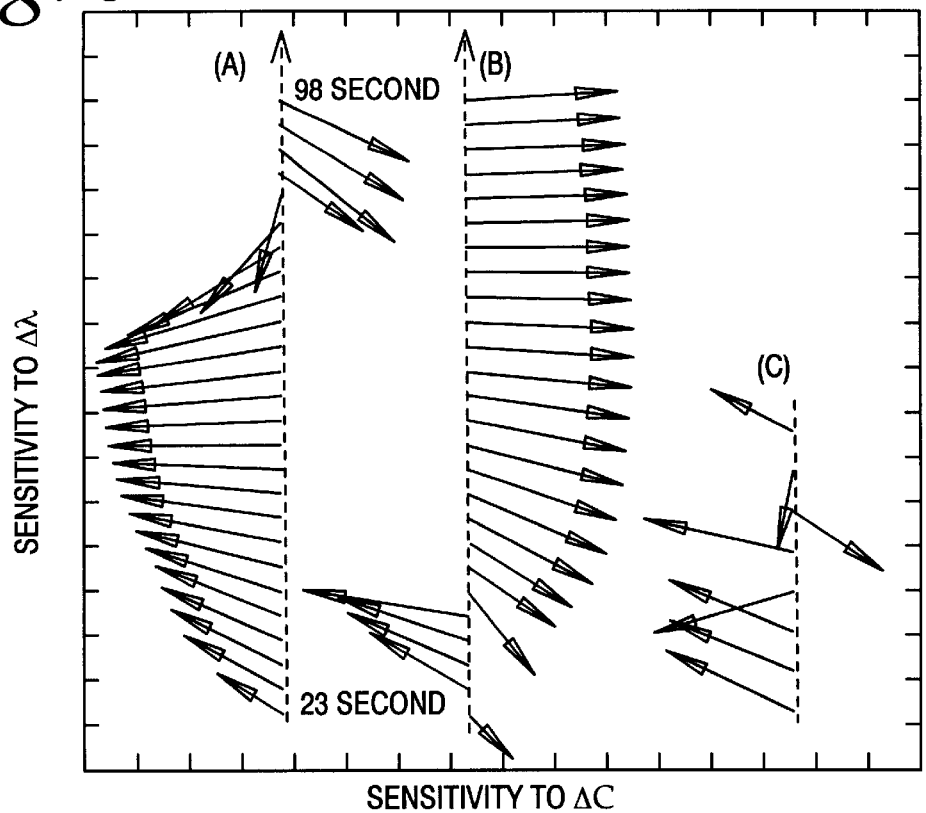
FIG. 9 is a graph of sensitivity vectors for five characteristic parameters.

FIG. 9 shows a plot of the sensitivity vectors for the actual calorimeter. Good qualitative agreement between the model and the actual calorimeter is evident upon examination of FIGS. 8 and 9. Due to the curvatures in the calibration surfaces, sensitivity maps change slightly in different regions of the thermal properties. FIG. 9 is constructed for water-like samples. The large vector magnitudes and notable inter-vector angles are essential for the ultra-high measurement precision of the calorimeter.

Figure 10A:
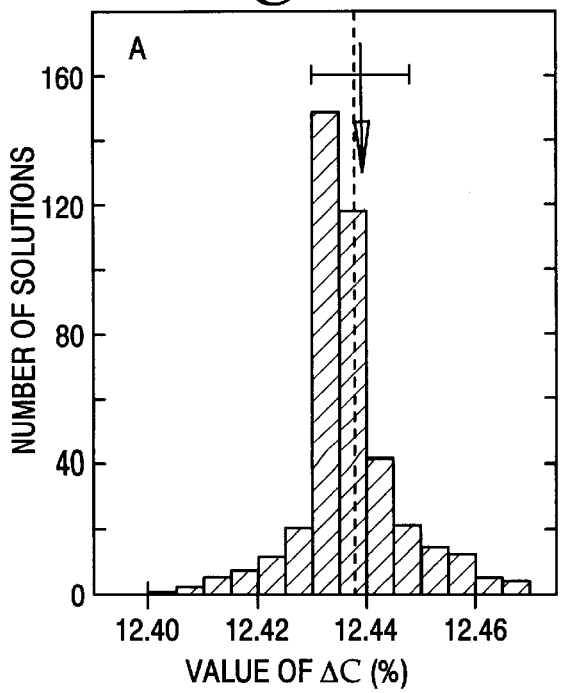
FIGS. 10A–10B are histogram distributions of filtered solutions (approximately 500 values for $\Delta C$ and $\alpha \lambda$).
Figure 10B:
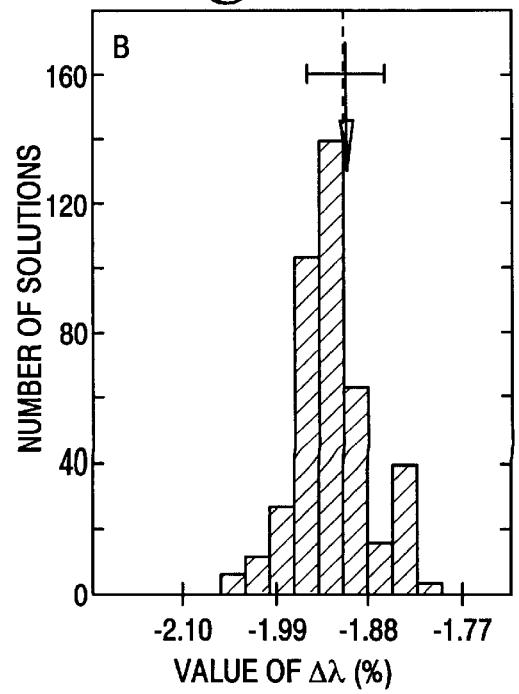

An example of a simultaneous measurement was performed with $D_2O$ in the sample cell and pure water in the reference cell. The differential response at 25° c was recorded and reproducible within system noise of the order of 10 nV. From the characteristic parameter values, the solutions for $\Delta C$ and $\Delta \lambda$ were obtained for each pair of parameters. These solutions were sorted according to their probable uncertainty. Sorting criteria resulted in keeping only about $\frac{1}{3}$ of the total solutions with small estimated uncertainties. This dynamic filtering of solutions effectively eliminates contributions from parameters having particularly small sensitivity indicator values and from pairings of parameters having nearly parallel sensitivity vectors at the thermal properties of the samples. FIG. 10 shows a histogram of the filtered solutions (about 500 values for each of $\Delta C$ and $\Delta \lambda$). The dashed vertical lines correspond to the simple average of the 400–500 individual values, and the error bars denote the standard deviation widths of the histogram. The vertical arrow points to the standard reference values used. The distributions have nice bell shapes and are strikingly narrow with standard deviation widths of only 0.009% and 0.045% of the corresponding heat capacity and thermal conductivity reference values for pure water. Since the filtered solutions all have similar uncertainties, simple averaging was used to get the best estimate for the final measurement values and the respective histogram widths as the measurement precision.

Figure 11:
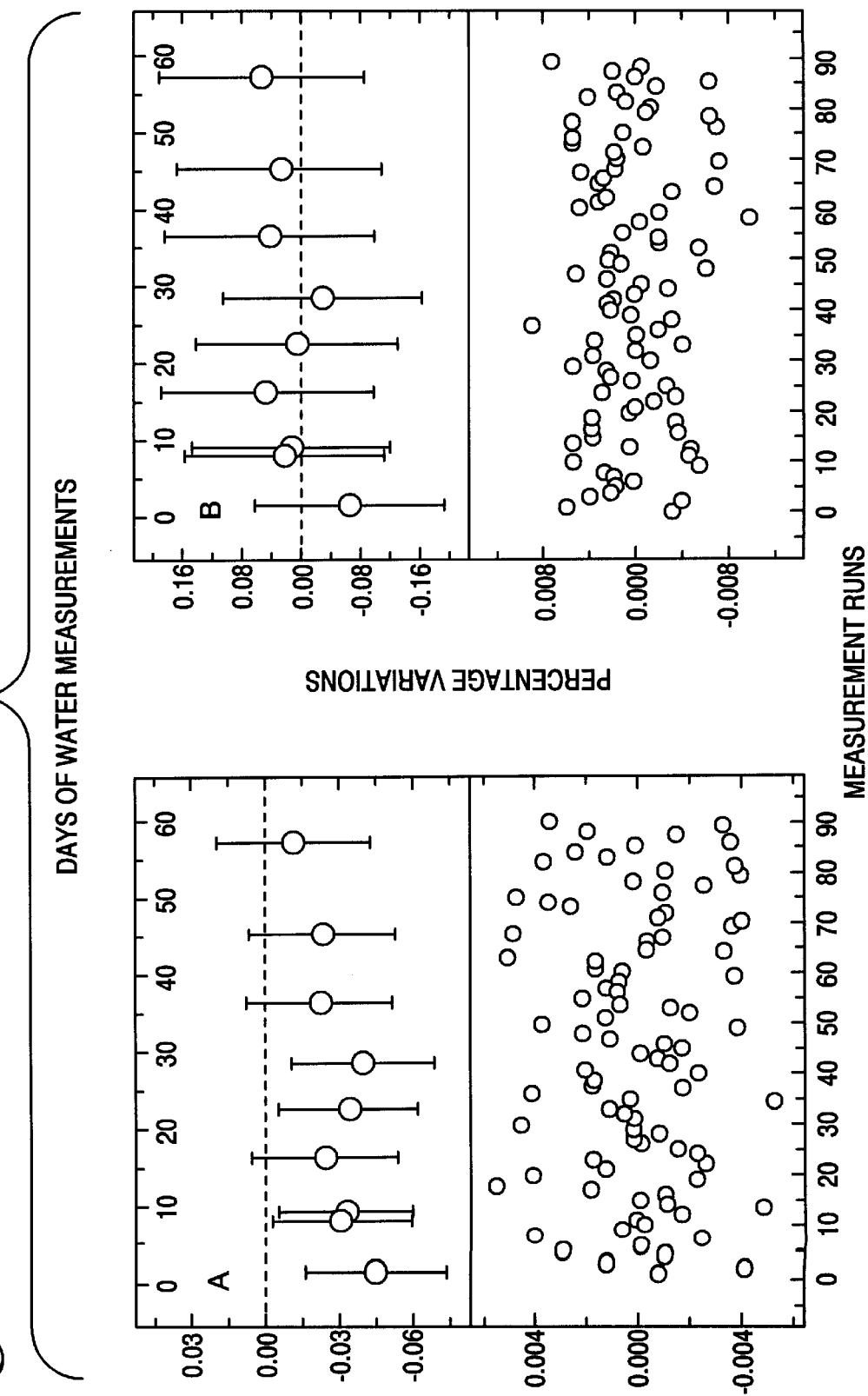
FIG. 11 are graphs of long-term stability and run-to-run reproducibility of calorimetry measurements for water.

Long term stability and run-to-run reproducibility of the calorimeter is shown in FIG. 11. Panel A shows the results of heat capacity and panel B shows the results of thermal conductivity for nine groups of measurements on pure water. Each group of results consists of ten consecutive measurements each lasting 500 seconds. The top parts of both panels show the mean value of the best estimate, together with the standard deviation width of the solution histogram (FIG. 10), for each group plotted against measurement date. The overall agreement is excellent with heat capacity and thermal conductivity deviations ranging from −0.047% to +0.013% and from −0.064% to +0.054%, respectively. The slight undulations and upward drifts of ±0.03% for heat capacity and ±0.05% for thermal conductivity over the two-month period are adequately covered by the solution histogram widths of about 0.03% and 0.14%, respectively. The bottom parts of both panels, on the other hand, show the run-to-run variations within each measurement group. The standard deviations associated with these spreads are 0.0025% and 0.0046%, respectively, for heat capacity in panel A and thermal conductivity in panel B. These run-to-run resolution limits of the measurement by the calorimeter are therefore, about a factor of ten to twenty smaller than the corresponding solution widths of the solution histograms.

Since each of the nine groups of measurements has entailed a separate filling of the water sample, these small variations in the results also demonstrate that filling errors are negligible. Indeed, repeat fillings at nearby dates using the partial vacuum procedure reveal no changes beyond run-to-run variations shown above. The long-term drift can be corrected by recalibration.

Figure 12:
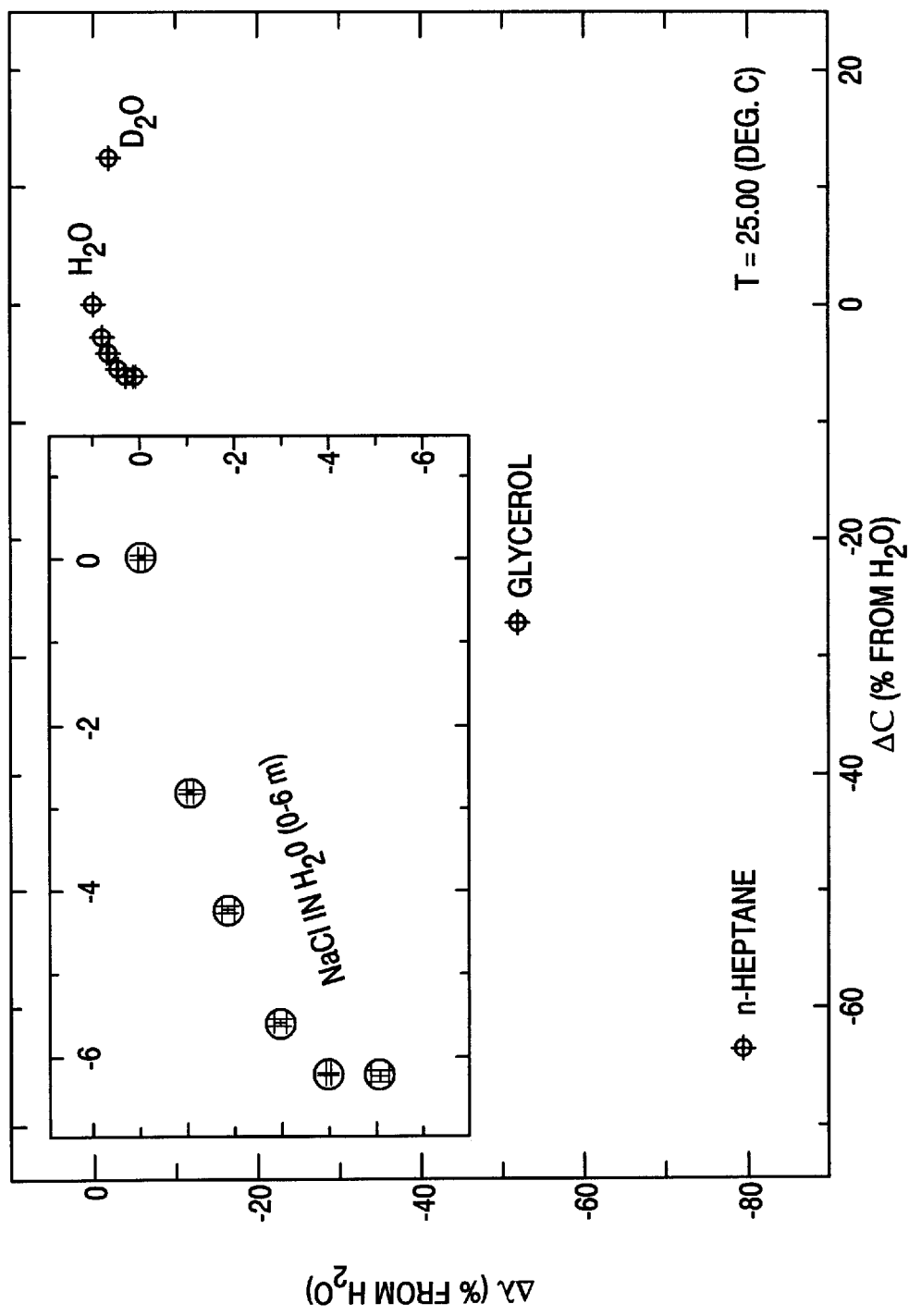
FIG. 12 shows the agreement between the best estimates and the respective standard values used for calibrations in the two-dimensional ($\Delta C$, $\Delta \lambda$) space.

The differential responses for the other calibration solutions at 25° C. were measured and heat capacity and thermal conductivity calculated. FIG. 12 shows the obtained agreement between the best estimates and the respective standard values that were used for the calibrations in the two-dimensional space ($\Delta C$, $\Delta \lambda$). The error bars are the standard deviation widths of the solution histograms; they correspond to the differences between the measured estimates and the standard values (see also FIG. 11). Note that the error sizes (i.e., the spread between parallel end bars) are only visible for the NaCl/water solutions (see insert, FIG. 12). Clearly, the agreement is across the whole region of thermal properties for fluid samples that are likely to be encountered.

A precision calorimeter for the simultaneous measurement of heat capacity and thermal conductivity has been described. The calibration accuracy can be gauged by the solution histogram width obtained directly from the measurement. The calorimeter provides accuracy of the order of one part in ten thousand for both heat capacity and thermal conductivity. For repeat measurements on stable samples, the run-to-run variations of the measurement for both heat capacity and thermal conductivity are about one part in one hundred thousand.

While there have been illustrated and described particular embodiments of the invention, it will be appreciated that numerous changes and modifications will occur to those skilled in the art, and it is intended in the appended claims to cover all those changes and modifications which fall within the true spirit and scope of the invention.

What is claimed is:

1. A method of simultaneously measuring thermal conductivity, $\lambda$, and heat capacity, C, of a fluid, comprising the steps of:

providing a heat conduction calorimeter having a first cell for receiving a reference fluid and a second cell for receiving a sample fluid;

calibrating the calorimeter using the reference fluid and at least one standard fluid having known thermal conductivity and heat capacity over a range of temperature to determine a set of sensitivity coefficients, $\{a_n^{ij}\}$, of the calorimeter, wherein the $a_n^{ij}$ are functions of the calorimeter, temperature and the reference fluid;

applying a square wave heat pulse to said calorimeter containing a sample fluid and said reference fluid;

measuring a thermal response curve to the square wave heat pulse, wherein the thermal response curve is a function of time, temperature of the measurement, thermal properties of the sample fluid and thermal properties of the reference fluid;

reducing the response curve to a set of characteristic parameters, $\{p_n\}$ wherein each $p_n$ is a function of time, temperature of the measurement, thermal properties of the sample fluid and thermal properties of the reference fluid; and calculating the thermal conductivity and heat capacity of the sample fluid from the $\{p_n\}$ for the sample fluid and the $\{a_n^{ij}\}$ for the calorimeter.

2. The method of claim 1 wherein the reference fluid is water.

3. The method of claim 1 wherein the standard fluid is selected from the group consisting of water, aqueous NaCl solutions, $D_2O$, n-heptane and glycerol.

4. The method of claim 1 wherein the sensitivity coefficients $\{a_n^{ij}\}$ are determined in accordance with the following relationship:

$$p_n = \sum_{i,j=0}^{Q} (a_n^{ij}(T) \Delta C^i \Delta \lambda^j),$$

where $a_n^{ij}(T)$=set of sensitivity coefficients for $p_n$, $\Delta C = (C_{samp}/C_{ref} - 1)/100$=percent change from the reference value of C, $\Delta \lambda = (\lambda_{samp}/\lambda_{ref} - 1)/100$=percent change from the reference value of $\lambda$, $\lambda_{ref}(T)$=thermal conductivity of the reference as a function of T, and $C_{ref}(T)$=volumetric heat capacity of the reference as a function of T.

5. The method of claim 1 wherein the $\{p_n\}$ are expressed as a set of closed form equations and the $\{a_n^{ij}\}$ are determined by solution thereof.

6. The method of claim 1 wherein said heat conduction calorimeter comprises:

a first cell including a first chamber for containing a reference material, a first heater element disposed within said chamber for heating said reference material, and first and second temperature sensors, disposed on opposite sides of said first chamber to eliminate air gaps between said first chamber and said first and second sensors and to minimize movement therebetween, for measuring the temperature at the respective interface between said first chamber and said first and second sensors;

a second cell including a second chamber for containing a sample material, a second heater element disposed within said second cell for heating said sample material, and third and fourth temperature sensors, disposed on opposite sides of said second chamber to eliminate air gaps between said second chamber and said third and fourth sensors and to minimize movement therebetween, for measuring the temperature at the respective interface between said second chamber and said third and fourth sensors;

partial vacuum means for filling said first and second cells with said reference material and said sample material, respectively;

a heat sink disposed about said first and second cells; and a fifth temperature sensor disposed within the heat sink for measuring the core temperature of the calorimeter;

wherein said first and second cells are rigidly mounted to each other to minimize movement in the sensor pathway.

7. The method of claim 1 wherein the step of calculating the thermal conductivity and heat capacity of the sample fluid comprises the substep of solving the following relationships:

$$\sum_{i+j=0}^{Q} (a_n^{ij}(T) \Delta C^i \Delta \lambda^j) = p_n,$$

where $a_n^{ij}(T)$ are known from the calibration step and $p_n$ is known from the measuring step.

8. The method of claim 1 wherein the providing step includes the substep of filling said first and second cells under a partial vacuum.

9. The method of claim 8 wherein the partial vacuum filling step includes the substeps of:

(a) filling the first and second cells under a partial vacuum above the vapor pressure of the respective fluid;

(b) after filling, returning the first and second cells to at least atmospheric pressure, thereby reducing the volume of any trapped gas bubbles.

10. The method of claim 9 wherein said measurement step further includes the substep of completing the measurement upon return of the first and second cells to at least atmospheric pressure, whereby heat capacity at constant pressure or constant volume and thermal conductivity are measured simultaneously.

11. A heat conduction calorimeter for simultaneously measuring the thermal conductivity and heat capacity of a fluid, comprising:

a first cell including a first chamber for containing a reference material, a first heater element disposed within said chamber for heating said reference material, and first and second temperature sensors, disposed on opposite sides of said first chamber to eliminate air gaps between said first chamber and said first and second sensors and to minimize movement therebetween, for measuring the temperature at the respective interface between said first chamber and said first and second sensors;

a second cell including a second chamber for containing a sample material, a second heater element disposed within said second cell for heating said sample material, and third and fourth temperature sensors, rigidly disposed on opposite sides of said second chamber to eliminate air gaps between said second chamber and said third and fourth sensors and to minimize movement therebetween, for measuring the temperature at the respective interface between said second chamber and said third and fourth sensors;

partial vacuum means for filling said first and second cells with said reference material and said sample material, respectively;

a heat sink disposed about said first and second cells; and a fifth temperature sensor disposed within the heat sink for measuring the core temperature of the calorimeter;

wherein said first and second cells are rigidly mounted to each other to minimize movement in the sensor pathway.

12. The calorimeter of claim 11 wherein said first, second, third and fourth temperature sensors are electrically coupled together for measuring the differential temperature response between said first and second cells.

13. The calorimeter of claim 12 wherein each of said first, second, third and fourth temperature sensors comprises four thermopiles.

14. The calorimeter of claim 11 wherein said partial vacuum means includes first and second tubing connected to said first and second chambers, respectively, wherein said first and second tubing extends outside said calorimeter.

15. The calorimeter of claim 14 wherein said tubing comprises tantalum tubing.

16. The calorimeter of claim 11 further comprising a preamplifier for preamplifying output signals generated by said first, second, third and fourth temperature sensors.

17. The calorimeter of claim 11 wherein said first and second cells are rigidly mounted to said heat sink.

* * * * *